(12) United States Patent
Swan et al.

(10) Patent No.: US 8,586,731 B2
(45) Date of Patent: Nov. 19, 2013

(54) HYDROPHOBIC POLYSACCHARIDES WITH DIESTER- OR CARBONATE ESTER-CONTAINING LINKAGES HAVING ENHANCED DEGRADATION

(75) Inventors: Dale G. Swan, St. Louis Park, MN (US); Emily R. Rolfes Meyering, Eden Prairie, MN (US); Aleksey V. Kurdyumov, Maplewood, MN (US); Stephen J. Chudzik, St. Paul, MN (US); Pamela J. Reed, legal representative, St. Paul, MN (US)

(73) Assignee: Surmodics, Inc., Eden Prairie, MN (US)

( * ) Notice: Subject to any disclaimer, the term of this patent is extended or adjusted under 35 U.S.C. 154(b) by 258 days.

(21) Appl. No.: 12/814,109

(22) Filed: Jun. 11, 2010

(65) Prior Publication Data

US 2010/0316687 A1 Dec. 16, 2010

Related U.S. Application Data

(60) Provisional application No. 61/268,346, filed on Jun. 11, 2009, provisional application No. 61/247,395, filed on Sep. 30, 2009.

(51) Int. Cl.
C07H 3/00 (2006.01)
A61F 13/00 (2006.01)

(52) U.S. Cl.
USPC ...................................... 536/123.1; 424/422

(58) Field of Classification Search
None
See application file for complete search history.

(56) References Cited

U.S. PATENT DOCUMENTS

| | | | |
|---|---|---|---|
| 4,011,392 | A | 3/1977 | Rudolph et al. |
| 5,459,258 | A | 10/1995 | Merrill et al. |
| 5,470,581 | A | 11/1995 | Grillo et al. |
| 5,869,647 | A | 2/1999 | Narayan et al. |
| 6,007,614 | A | 12/1999 | Billmers et al. |
| 6,528,642 | B1 | 3/2003 | Duval et al. |
| 6,562,961 | B1 | 5/2003 | Seeger et al. |
| 7,919,111 | B2 | 4/2011 | Chudzik et al. |
| 2002/0123624 | A1 | 9/2002 | Qiao et al. |
| 2004/0037886 | A1 | 2/2004 | Hsu |
| 2005/0019371 | A1 | 1/2005 | Anderson et al. |
| 2005/0255142 | A1 | 11/2005 | Chudzik et al. |
| 2006/0249705 | A1 | 11/2006 | Wang et al. |
| 2007/0065481 | A1 | 3/2007 | Chudzik et al. |
| 2007/0218102 | A1 | 9/2007 | Chudzik et al. |
| 2007/0224247 | A1 | 9/2007 | Chudzik et al. |
| 2007/0260054 | A1 | 11/2007 | Chudzik |
| 2010/0093662 | A1 | 4/2010 | Defaye et al. |
| 2010/0099861 | A1 | 4/2010 | Okamoto et al. |
| 2010/0303879 | A1 | 12/2010 | Kurdyumov et al. |
| 2011/0076314 | A1 | 3/2011 | Kurdyumov |
| 2011/0076337 | A1 | 3/2011 | Slager et al. |
| 2011/0159067 | A1 | 6/2011 | Rolfes Meyering |

FOREIGN PATENT DOCUMENTS

| | | |
|---|---|---|
| EP | 0 405 917 | 1/1991 |
| JP | 2001/321094 | 3/2001 |
| WO | 02/094224 | 11/2002 |

OTHER PUBLICATIONS

Péan, et al. (1999) *Why Does PEG 400 Co-Encapsulation Improve NGF Stability and Release from PLGA Biodegradable Microspheres?* Pharmaceutical Research 16: 1294-1299.

Varela, et al., (2005) *Evaluation of biochemical analytes in vitreous humor collected after death in West Indian manatees*, JAVMA 226: 88-92.

Chen, et al., (1995) *Enzymatic and chemoenzymatic approaches to synthesis of sugar-based polymer and hydrogels*, Carbohydrate Polymers 28: 15-21.

van Veen, et al. (2005) *The Effect of powder blend and tablet structure on drug release mechanisms of hydrophobic starch acetate matrix tablets*, European Journal of Pharmaceutics and Biopharmaceutics 61: 149-157.

Tarvainen, et al. (2004) *Aqueous starch acetate dispersion as a novel coating material for controlled release products*, Journal of Controlled Release 96: 179-191.

Magdassi, et al. (2001) *Interfacial Properties of Hydrophobically Modified Biomolecules: Fundamental Aspects and Applications*, J. Dispersion Science and Technology 22: 313-322.

Na, et al. (2003) *Self-assembled nanoparticles of hydrophobically-modified polysaccharide bearing vitamin H as a targeted anti-cancer drug delivery system*, European Journal of Pharmaceutical Sciences 18: 165-173.

Uekama, K. (2004) *Pharmaceutical Application of Cyclodextrins as Multi-functional Drug Carriers*, Yakugaku Zasshi 124: 909-935.

Kaur, et al. (2004) *Role of Cyclodextrins in Ophthalmics*, Current Drug Delivery 1: 351-360.

*Primary Examiner* — David J Blanchard
*Assistant Examiner* — Tigabu Kassa
(74) *Attorney, Agent, or Firm* — Kagan Binder, PLLC

(57) ABSTRACT

Hydrophobic α(1→4)glucopyranose polymers with enhanced degradation properties are described. Between the α(1→4)glucopyranose polymeric portion and the hydrophobic portion exists a linker portion having a chemistry that facilitates degradation of the polymer. Diester and carbonate ester linker chemistries are exemplified. Biodegradable matrices can be formed from these polymers, and the matrices can be used for the preparation of implantable and injectable medical devices wherein the matrix is capable of degrading in vivo at an increased rate. Matrices including and capable of releasing a bioactive agent in vivo are also described.

13 Claims, No Drawings

HYDROPHOBIC POLYSACCHARIDES WITH DIESTER- OR CARBONATE ESTER-CONTAINING LINKAGES HAVING ENHANCED DEGRADATION

PRIORITY CLAIM

This application claims the benefit of U.S. Provisional Patent Application Ser. No. 61/268,346 filed Jun. 11, 2009, entitled HYDROPHOBIC POLYSACCHARIDES WITH DIESTER-CONTAINING LINKAGES HAVING ENHANCED DEGRADATION and U.S. Provisional Patent Application Ser. No. 61/247,395 filed Sep. 30, 2009, entitled HYDROPHOBIC POLYSACCHARIDES WITH CARBONATE ESTER-CONTAINING LINKAGES HAVING ENHANCED DEGRADATION the disclosure of which is incorporated herein by reference.

TECHNICAL FIELD

The present invention relates to hydrophobic polysaccharides, and medical articles formed from these hydrophobic polysaccharides for use within the body.

BACKGROUND

Biodegradable polymers have been used to prepare biodegradable polymeric matrices that can be associated with, or formed into, implantable medical devices. For example, biodegradable polymers can be used to make a thin coating on the medical device's surface, generally designed to enhance the function of the device. Biodegradable polymers having thermoplastic properties can even be molded or formed into a shape to provide an implantable device having a structural property useful for treating a medical condition at the site of implantation. In theory, the polymeric matrix becomes completely degraded in the body. This can be advantageous for various medical applications, for example, such as to eliminate the requirement for explanation of the implanted article.

Implantable articles having biodegradable polymeric matrices can also be used to modulate the delivery of drugs to a patient at the site of implantation. Drug-releasing biodegradable matrices can be in the form of a coating on a device, or in the form of an implantable or injectable article that is formed primarily of the biodegradable polymer. Drug contained within the biodegradable matrix can be released or eluted from the matrix after the article has been introduced into the body.

The current invention relates to biodegradable polymeric matrices made using hydrophobic $\alpha(1\to 4)$glucopyranose and overcomes challenges in the art and represents improvements with regards to properties such as biocompatibility and biodegradability of materials of implantable or injectable medical articles.

SUMMARY OF THE INVENTION

Generally, the present invention relates to hydrophobic polysaccharides with chemistries that promote increased degradation of matrices formed from these polymers. The invention also relates to polymeric matrices formed from these polymers, articles including these polymeric matrices, and methods for using these matrices, such as for the treatment of a medical condition.

In one aspect, the invention provides a hydrophobic $\alpha(1\to 4)$glucopyranose polymer a linker portion having a chemistry that facilitates degradation of the polymer.

Generally, the polymer includes a poly-$\alpha(1\to 4)$glucopyranose portion and a plurality of groups pendent from the poly-$\alpha(1\to 4)$glucopyranose portion, the groups including a hydrocarbon segment. The hydrocarbon segments provide hydrophobic properties to the polymer. In some aspects, between a monomeric unit of the poly-$\alpha(1\to 4)$glucopyranose portion and the hydrocarbon segment in a pendent group is a linker segment which includes two or more hydrolytically cleavable groups selected from ester and ester-containing groups.

In other aspects, between a monomeric unit of the poly-$\alpha(1\to 4)$glucopyranose portion and the hydrocarbon segment in a pendent group is a linker segment that includes a carbonate ester group.

The presence of two or more ester or ester containing groups in the linker region, or a carbonate ester group in the linker region, can enhance the rate of degradation of matrices and provide improved implantable or injectable medical articles with a polymeric matrix designed to degrade at a target location in the body over a period of time.

In some aspects, the hydrophobic $\alpha(1\to 4)$glucopyranose polymer has a pendent group including linker and hydrocarbon segments, the linker portion including two hydrolytically cleavable groups selected from ester and ester-containing groups according to Formula I:

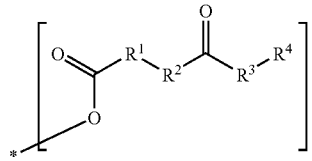

In formula I, $R^4$ is a $C_2$-$C_{18}$ hydrocarbon group. Also, one of arrangements (a) or (b) is used. In arrangement (a) $R^1$ is $R^5$, and either (i) one or both of $R^2$ and/or $R^3$ is O (with the proviso that if only one of $R^2$ or $R^3$ is O, then the other is a covalent bond), or (ii) $R^2$ or $R^3$ is O, with the other being S. In arrangement (b) $R^1$ is O or S, $R^2$ is $R^5$, $R^5O$, or $R^5S$, and $R^3$ is O or S (with the proviso that if $R^2$ is $R^5S$ or $R^3$ is S, then $R^3$ is O or $R^2$ is $R^5O$, respectively). In both (a) and (b) $R^5$ is a $C_1$-$C_{12}$ hydrocarbon group.

In some aspects, the hydrophobic $\alpha(1\to 4)$glucopyranose polymer has a pendent group including a carbonate ester-containing linker segment and hydrocarbon group according to Formula VIII:

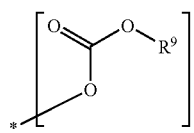

wherein $R^9$ is a $C_1$-$C_{18}$ hydrocarbon group. In exemplary formulations, $R^9$ is includes a linear, branched, or cyclic $C_2$-$C_{18}$ hydrocarbon group.

Optionally, and in addition to pendent groups having a linker groups that includes either a carbonate ester group or at least two ester or ester-containing groups, the hydrophobic $\alpha(1\to 4)$glucopyranose polymer can include one or more additional pendent group(s) (e.g., second pendent groups) comprising a hydrocarbon group, the hydrocarbon group which is linked to the poly-$\alpha(1\to 4)$glucopyranose portion via a linker segment that contains a group other than either the carbonate ester group or the two ester or ester-containing groups. Other types of groups that can be included in the linker segment of the second pendent groups include ester, thioester, silyl ether, and carbamate.

As a general matter, biodegradable polymeric matrices can be formed from these hydrophobic α(1→4)glucopyranose polymers having these inventive linker chemistries. The matrices can be in various forms. These forms include microparticles, a coated layer on a device surface, or a three-dimensional implant. In some cases, the matrices can be associated with an implantable article, which can be fabricated from a material that is different that the biodegradable polymers of the invention.

Therefore, in other aspects, the invention provides an implantable or injectable biomedical article, the article comprising a polymeric matrix comprising hydrophobic α(1→4) glucopyranose polymers having pendent groups which include a hydrocarbon segment that and a linker group comprising two or more ester or ester-containing groups, or a carbonate ester group.

Articles formed from or associated with polymeric matrices formed from the hydrophobic α(1→4)glucopyranose polymers can be introduced into the body. The matrices can be placed at a target location in a subject (i.e., in vivo). After a period of time, the polymeric matrix can degrade. Matrices formed from hydrophobic α(1→4)glucopyranose polymers with linker portions that include two or more ester groups, or a carbonate ester group, can exhibit faster rates of degradation, allowing for the degradation of the matrix in a shorter period of implantation. This can be beneficial for drug delivery applications. It also can be beneficial where a structural feature of the biodegradable implant is used to treat a medical condition, and the treatment is short-term. The enhanced degradation is thought to be cause by increased susceptibility of the linker regions containing either two ester or ester-containing groups, or the carbonate ester group, to non-enzymatic hydrolytic attack. Non-enzymatic hydrolysis cleaves the pendent groups at both ester linkages, or the carbonate ester linkage, and causes loss of the groups containing the hydrocarbon segments. This, in turn, reduces the hydrophobicity of the matrix and further promotes non-enzymatic hydrolysis. Loss of the hydrocarbon segment also increases susceptibility of the α(1→4)glucopyranose portion to enzymatic degradation by amylases. The hydrophobic polysaccharides can be degraded into natural materials, which provide advantages for compatibility of implantable articles. Degradation of the matrix can result in the release of, for example, naturally occurring mono- or disaccharides, such as glucose, which are common serum components.

In some aspects the polymeric matrix formed from the hydrophobic α(1→4)glucopyranose polymer is included in a implantable or injectable medical article capable of releasing one or more bioactive agent(s) in a subject. The hydrophobic α(1→4)glucopyranose polymer can be used in association with the device to modulate or facilitate preparation of an article that includes and is capable of releasing the one or more bioactive agent(s). For example, in some aspects a bioactive agent can be present within the matrix formed from the hydrophobic α(1→4)glucopyranose polymer. Bioactive agent can be released from the matrix by elution out of the matrix, degradation of the matrix material, or both. Since the matrix can be completely degraded, the total amount of the bioactive agent contained in the matrix can be made available to the subject after a period of implantation. This allows the implants to be particularly useful for the treatment of medical conditions that require therapeutically effective amounts of a bioactive agent over a defined period of treatment.

In other aspects, the polymeric matrix formed from the hydrophobic α(1→4)glucopyranose polymer is in the form of a bioactive agent release barrier on an implantable article, such as a polymeric top coat, or an encapsulating shell around a microparticle. Prior to degradation of the release barrier, release of one or more bioactive agent(s) is restricted or largely prevented. Following implantation or injection, the barrier layer is capable or degrading in a shorter, defined period of time, after which most or all of the bioactive agents are released and made available to the subject.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to hydrophobic α(1→4)glucopyranose polymers with groups pendent from the α(1→4)glucopyranose backbone, and polymeric matrices formed therefrom.

In one aspect, the hydrophobic α(1→4)glucopyranose polymer comprises pendent groups which include a hydrocarbon segment that is linked to the α(1→4)glucopyranose backbone with a linker segment that include two or more ester or ester-containing groups. In another aspect, the pendent groups include a hydrocarbon segment which is linked to the monomeric unit of the α(1→4)glucopyranose polymers via a linker segment that includes a carbonate ester group.

The invention is also directed to compositions including these hydrophobic α(1→4)glucopyranose polymers, articles that are formed using these hydrophobic α(1→4)glucopyranose polymers, and methods for using articles formed from these polymers, such as drug delivery methods for the treatment of a medical condition.

As a general matter, the hydrophobic α(1→4)glucopyranose polymer can be considered to have at least two main parts. The first part is an α(1→4) glucopyranose polymeric backbone. The second part is a group (or generally a plurality of groups) pendent from the α(1→4)glucopyranose polymeric backbone (also referred to herein as "pendent groups"). In many modes of practice, the pendent groups are added to the backbone of a natural α(1→4)glucopyranose polymer through a chemical derivation process. The pendent group comprises at least one hydrocarbon segment comprising one or more carbon atoms, or two or more carbon atoms. The amount and type of the hydrocarbon segments present in the pendent groups can provide sufficient hydrophobicity to the modified α(1→4)glucopyranose polymer. Therefore, in many aspects, the sum amount of the hydrocarbon segments among the pendent groups constitute the hydrophobic portion of the polymer. In some preparations, the poly-α(1→4)glucopyranose portion and the hydrophobic portion can present at a weight ratio of 2:1 or greater (33 wt % or greater), respectively, such as in the range of about 2:1 to about 1:10, respectively, or in the range of about 1:1 to about 1:5, respectively.

Generally, a pendent group will include at least one hydrocarbon segment which is positioned at the end of a respective pendent group (i.e., distal from the α(1→4)glucopyranose polymer backbone). The pendent groups also include a linker portion between the distal hydrocarbon group and the glucopyranose monomeric units.

In one aspect of the invention, the linker portion includes two or more hydrolytically cleavable ester or ester-containing groups. As used herein, an "ester group" in the linker portion includes at least the essential group:

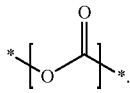

In some aspects, the two or more groups in the linker portion include the essential ester group, and at least one organic heteroatom(s) bonded to the carbonyl carbon of the ester group. An ester containing-group is exemplified by Formula II, wherein X is independently selected from an organic heteroatom:

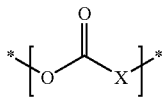

Exemplary ester-containing groups include carbonate ester and thioester, wherein X is either O or S, shown respectively below:

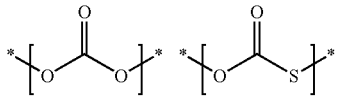

The ester or ester-containing groups (e.g., carbonate ester or thioester groups) have the common feature of being hydrolyzable, although different ester and ester-containing groups may be subject to hydrolysis at different rates (e.g., a thioester hydrolyzes faster than an ester).

In another aspect of the invention, the linker portion includes a carbonate ester group.

Overall, the hydrophobic α(1→4)glucopyranose polymer displays hydrophobic properties. The polymer can be used to form a hydrophobic α(1→4)glucopyranose matrix, such as in the form of a degradable coating or an implantable drug delivery device.

In a pendent group, the hydrocarbon segment comprising one or more carbon atoms can include a saturated hydrocarbon segment or an unsaturated hydrocarbon segment. The pendent group can also include a combination of saturated and unsaturated hydrocarbon groups. Examples of hydrocarbon groups include linear and branched alkyl, alkenyl, alkynyl, as well as cyclic alkyl, cyclic alkenyl, aromatic hydrocarbon, and aralkyl groups The hydrocarbon segment can be a monovalent hydrocarbon radical, such as a group of covalently bonded carbon atoms having the formula —$(CH_n)_m$—$CH_3$, wherein m is 1 or greater, and n is independently 2 or 1. A monovalent hydrocarbon radical can be positioned at the terminus of the pendent group (i.e., distal from the polysaccharide backbone). In some aspects, a monovalent hydrocarbon radical can be positioned at the terminus of the pendent group (i.e., distal from the polysaccharide backbone) and covalently bonded to the carbonate ester group.

The hydrocarbon segment can be a divalent hydrocarbon radical, such as a group of covalently bonded carbon atoms having the formula —$(CH_n)_m$—, wherein m is 1 or greater, and n is independently 2 or 1. A divalent hydrocarbon radical can be positioned between the terminus of the pendent group and the polysaccharide backbone. If the pendent group includes a hydrocarbon segment that is a divalent hydrocarbon radical, it can be separated from another hydrocarbon segment by a carbon of a non-hydrocarbon group, or an organic heteroatom. In some aspects, the pendent group includes two hydrocarbon segments that are separated from each other in the pendent group by an ester or ester-containing group.

For example, the pendent group can also include a second hydrocarbon segment (the first hydrocarbon group being the distally-located hydrocarbon group). The second hydrocarbon group can be located between one (e.g., a first) ester or ester-containing group, and another (e.g., a second) ester or ester-containing group. If present, a second hydrocarbon group can contribute to the hydrophobic portion of the hydrophobic α(1→4)glucopyranose polymer.

In some aspects, a divalent hydrocarbon radical can be positioned between a carbon of a non-hydrocarbon group, or an organic heteroatom, and a carbonate ester group.

In some aspects, the hydrocarbon segment comprises a linear, branched, or cyclic group containing two or more carbon atoms. In some aspects, the hydrocarbon segment is a $C_1$-$C_{18}$-containing, a $C_1$-$C_{10}$-containing, a $C_4$-$C_8$-containing, or a $C_4$-$C_5$-containing linear, branched, or cyclic hydrocarbon group.

An α(1→4)glucopyranose polymer, which forms the poly-α(1→4)glucopyranose portion of the hydrophobic α(1→4) glucopyranose polymer, includes repeating α-D-glucopyranose ($Glc_p$) monomers having α(1→4) linkages. A portion (three monomeric units) of an α(1→4) glucopyranose polymer, without the pendent group, is shown below:

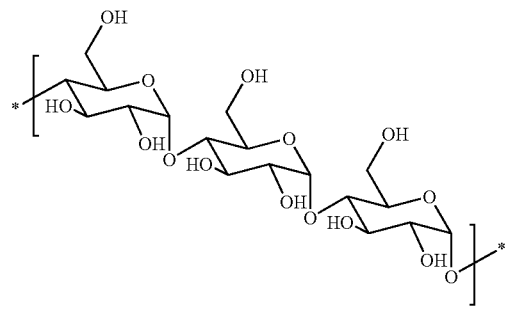

As starting material for the preparation of the diester-modified hydrophobic α(1→4)glucopyranose polymer, one can use exemplary α(1→4)glucopyranose polymers, such as maltodextrin, amylose, cyclodextrin, and polyalditol (polyalditol is available from GPC (Muscatine, Iowa) under the tradename Innovatol™ PD60, and has <1% reducing sugars). Maltodextrins generally refer to those polymer preparations having a lower molecular weight than amylose preparations. Cyclodextrins are low molecular weight cyclic α(1→4)glucopyranose polymers.

Maltodextrin is typically generated by hydrolyzing a starch slurry with a heat-stable α-amylase at temperatures at 85-90°

C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylase molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights are commercially available.

As used herein, "amylase" or "amylase polymer" refers to a linear polymer having repeating glucopyranose units that are joined by α-1,4 linkages. Some amylase polymers can have a very small amount of branching via α-1,6 linkages (about less than 0.5% of the linkages) but still demonstrate the same physical properties as linear (unbranched) amylase polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

Exemplary maltodextrin and amylase polymers have molecular weights ranging from about 500 Da to about 500,000 Da, about 1000 Da to about 300,000 Da, and about 5000 Da to about 100,000 Da.

Maltodextrin and amylose polymers of various molecular weights are commercially available from a number of different sources. For example, Glucidex™ 6 (ave. molecular weight ~95,000 Da) and Glucidex™ 2 (ave. molecular weight ~300,000 Da) are available from Rouquette (France); and MALTRIN™ maltodextrins of various molecular weights, including molecular weights from about 12,000 Da to 15,000 Da are available from GPC (Muscatine, Iowa).

The decision of using amylose of a particular size range may depend on factors such as the physical characteristics of the composition, the desired rate of degradation of the matrix formed from the polysaccharide, and the presence of other optional components in the matrix, such as bioactive agents.

Refinement of the molecular weight of a polymer preparation (such as the α(1→4)glucopyranose polymer starting material) can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

The polymers as discussed herein can be described in terms of molecular weight. "Molecular weight," as used herein, more specifically refers to the "weight average molecular weight" or $M_w$, which is an absolute method of measuring molecular weight and is particularly useful for measuring the molecular weight of a polymer (preparation). Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation (for example, the characteristics of an initiator polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry; pg* 271 (1990).

In forming the hydrophobic α(1→4)glucopyranose polymer, and in some modes of practice, a compound having a hydrocarbon group, and groups which provide two or more ester or ester-containing groups (after the compound is reacted to provide a pendent group), is covalently coupled a portion of an α(1→4)glucopyranose polymer. In some modes of practice, a compound having a hydrocarbon group, and a group which provides a carbonate ester group (after the compound is reacted to provide a pendent group), is covalently coupled a portion of an α(1→4)glucopyranose polymer. Typically, these compounds are reacted with the α(1→4)glucopyranose polymer to provide a plurality of pendent groups, the pendent groups present at a desired level of substitution on the α(1→4)glucopyranose polymer.

Optionally, an α(1→4)glucopyranose polymer can be prepared to have a combination of different linker group chemistries. For example, in some preparations, the α(1→4)glucopyranose polymer has a first set of pendent groups that include two or more ester groups, and a second set of pendent groups that includes a group other than an ester group. In other preparations, the α(1→4)glucopyranose polymer has a first set of pendent groups that includes a carbonate ester group, and a second set of pendent groups that includes a groups other than a carbonate ester group.

For example, the group in the second set of pendent groups that is different than the group in the first set can be selected from ester, carbonate ester, thioester, carbamate, and silyl ether.

In underivatized form, the glucopyranose units of a α(1→4)glucopyranose polymer includes monomeric units having glucopyranose ring structures with primary hydroxyl groups (the number 6 carbon on the glycopyranose ring) and secondary hydroxyl groups (the number 2 and 3 carbons on the glycopyranose ring). Primary and/or secondary hydroxyl groups can be reacted with a hydroxyl reactive compound to provide a pendent group that replaces the primary and/or secondary hydroxyl group on the glucopyranose monomeric unit. Generally, the primary (number 6 carbon) hydroxyl group is more reactive than the secondary hydroxyl group. Therefore, reaction with a limited quantity of reactive compound will form a hydrophobic α(1→4)glucopyranose polymer with more primary hydroxyls than secondary hydroxyls modified, or a portion of primary hydroxyls and no secondary hydroxyls modified Generally hydrophobic α(1→4)glucopyranose of claim 1 has a degree of substitution with pendent groups of 0.2 or greater, and more typically in the range of 0.5 to 2.5.

In some cases, one of the ester groups of the linker segment replaces one or more original hydroxyl group(s) on the glucopyranose monomeric unit. Pendent groups can be formed on positions on the glucopyranose monomeric units previously corresponding to either or both primary and/or secondary hydroxyl group locations. In many preparations more of the primary hydroxyl groups than secondary hydroxyl groups become derivatized with the pendent groups containing the hydrocarbon group and two or more ester or ester-containing groups.

As stated, the hydrophobic α(1→4)glucopyranose polymer can be formed by reacting a compound that includes a hydrocarbon group and groups that provide two or more ester groups, with a hydroxyl group on the glucopyranose monomeric unit. The compound can include a hydroxyl-reactive, ester-forming group. In other words, the hydroxyl-reactive, ester-forming group can form an ester or ester-containing group such as ester, carbonate, or thioester, when reacted with a primary or secondary hydroxyl group on the glucopyranose monomeric unit. For example, the compound can include (a) a hydrocarbon group at one end, (b) a hydroxyl-reactive, ester-forming group at the other end, and (c) an ester group, or ester-containing group positioned between groups (a) and (b).

Examples of ester-forming, hydroxyl-reactive groups (group b) that can provide an ester or ester-containing group when reacted with a hydroxyl group on the hydroxyl group of the glucopyranose unit include carboxyl, anhydride, acid halides, and the like. Other methods include two-step reactions of activating the hydroxyl groups followed by reaction by a reactive hydroxyl or thiol group to yield carbonates and thiol carbonates.

In some modes of practice the α(1→4)glucopyranose polymer is reacted with an alkyl succinate or alkyl maleate compound(s). Alkyl succinates and alkyl maleate are examples of compounds that have (a) a hydrocarbon group at one end, (b) hydroxyl-reactive, ester-forming group at the other end, and (c) an ester group positioned between groups (a) and (b).

Exemplary alkyl groups that can be present on alkyl succinates and alkyl malonates include ethyl, propyl, isopropyl, propyl, isopropyl, n-butyl, isobutyl, t-butyl, pentyl, cyclopentyl, hexyl, cyclohexyl, and octyl.

For example, suitable alkyl succinates include, but are not limited to ethyl succinate, propyl succinate, isopropyl succinate, propyl succinate, isopropyl succinate, n-butyl succinate, isobutyl succinate, t-butyl succinate, pentyl succinate, cyclopentyl succinate, hexyl succinate, cyclohexyl succinate, and octyl succinate.

Suitable alkyl maleates include, but are not limited to ethyl maleate, propyl maleate, isopropyl maleate, propyl maleate, isopropyl maleate, n-butyl maleate, isobutyl maleate, t-butyl maleate, pentyl maleate, cyclopentyl maleate, hexyl maleate, cyclohexyl maleate, and octyl maleate.

As a general matter, alkyl succinate and alkyl maleate compounds can be prepared by the reaction of an alkyl alcohol (e.g., butyl alcohol) with succinic anhydride (dihydro-2,5-furandione) or maleic anhydride (2,5-furandione). Some alkyl succinates and alkyl maleates can also be commercially obtained (for example, from Sigma Aldrich).

Compounds, such as alkyl succinates and alkyl maleates, provide pendent groups with hydrocarbon and two or more ester or ester-containing groups when reacted with hydroxyl groups of the monomeric units along the length of the α(1→4)glucopyranose polymer. The derivatized α(1→4) glucopyranose polymer can include derivatized glucopyranose monomeric unit having a pendent groups with hydrocarbon and two or more ester or ester-containing groups, as well as underivatized glucopyranose monomeric units.

Optionally, the hydrophobic poly(α(1→4)glucopyranose can be synthesized having a combination of pendent groups with hydrocarbon segment chemistries. For example, the hydrophobic polysaccharide can be synthesized using a mixture of alkyl succinates, the mixture including alkyl succinates having hydrocarbon groups with different alkyl chain lengths.

The amount of groups including the hydrocarbon and linker segments made pendent from the polymer backbone can be characterized by a degree of substitution (DS), which is defined as the average number of pendent groups linked to each sugar residue. Since each sugar residue in an α(1→4) glucopyranose polymer has three hydroxyls available for modification, DS values range from zero to three (full substitution).

The type of hydrocarbon segment present in the pendent can also influence the hydrophobic properties of the polymer. Generally, if compounds having large hydrocarbon groups (e.g., longer alkyl groups) are used for the synthesis of the hydrophobic polysaccharide, a smaller amount of the compound may be needed for reaction with the poly(α(1→4) glucopyranose to provide hydrophobicity. In other words, as the chain length of the alkyl group increases, the amount of the compound needed to provide a hydrophobic polysaccharide can decrease. Shorter hydrocarbon groups typically are substituted at a higher DS, whereas longer hydrocarbon group are typically substituted at a lower DS For example, if a compound (e.g., an alkyl succinate) having a hydrocarbon segment with an alkyl chain length of $C_x$ is used to prepare a hydrophobic polysaccharide with a DS of 1, a compound having a hydrocarbon segment with an alkyl chain length of $C_{(2x)}$ is reacted in an amount to provide a hydrophobic polysaccharide (with comparable hydrophobicity) with a DS of 0.5.

As an example, to provide a hydrophobic polysaccharide, isobutyl succinate (i.e., an alkyl chain length of 4) is reacted with poly(α(1→4)glucopyranose) to provide a degree of substitution of the hydroxyl groups of about 0.1 or greater, such as is in the range of about 0.5-2.5.

The degree of substitution can influence the hydrophobic character of the polysaccharide. In turn, polymeric matrices formed from diester-modified hydrophobic α(1→4)glucopyranose polymers having a high weight ratio of the hydrophobic portion to the α(1→4)glucopyranose polymer (as exemplified by a high DS) are generally more hydrophobic and can be more resistant to degradation. For example, a matrix formed from modified maltodextrin-diester isobutyrate DS 1.0 may have a rate of degradation that is faster than a matrix fainted from maltodextrin-diester isobutyrate DS 1.5.

In preparing the diester-modified hydrophobic α(1→4) glucopyranose polymer any suitable synthesis procedure can be performed. Synthesis can be carried out to provide a desired number of pendent groups containing the hydrocarbon and two or more ester or ester-containing groups pendent from the polysaccharide backbone. The number and/or density of the pendent groups can be controlled, for example, by controlling the relative concentration of the compound (e.g., an alkyl succinate) that provides the pendent groups to the available reactive groups (e.g., hydroxyl groups) on the polysaccharide.

The following general process outline steps describing reagent types and use of reagents in suggested ranges to provide a hydrophobic α(1→4)glucopyranose. In order to provide a desired product, one of skill could modify the process by substituting the cited reagents with similar reagents, in amounts appropriate to provide a hydrophobic polysaccharide.

Preparation of a diester-modified hydrophobic α(1→4) glucopyranose polymer can be carried out using a general esterification process as follows. In dry form, a molar excess of maltodextrin having a starting molecular weight in the range of about 1-500 kDa is combined with a carboxylic acid activating reagent and an organic base. An exemplary activating reagent is N-hydroxysuccinimide (NHS) and an exemplary organic base is N,N'-dimethylaminopyridine (DMAP), which can be used in about a molar amount of about 10 fold less than the molar amount of maltodextrin. The components can then be dissolved in a polar aprotic solvent, such as DMSO, to provide a concentration of maltodextrin of approximately 125 mg/mL. The mixture can then be heated (e.g., about 50° C. or greater) and stirred to dissolve the solids.

Next, a selected alkyl succinate (or combination of alkyl succinates) is added to the maltodextrin mixture in an amount to provide a desired level of polysaccharide derivation. As an example, butyl succinate is added to the maltodextrin mixture in an amount of approximately 15 mmol (of butyl succinate) per gram of maltodextrin. An amount of butyl succinate can be added to provide the α(1→4)glucopyranose polymer with a desired degree of hydrophobicity. Additional activating agent, such as N,N'-diisopropylcarbodiimide (DIC), can be added to the reaction. The maltodextrin can then be reacted with the butyl succinate at about room temperature for a period of time of greater than 2 hours.

Purification of the reaction product can be performed by the addition of water to the reaction solution, which causes precipitation of the diester-modified hydrophobic α(1→4) glucopyranose polymer. The precipitated polymer can then be dried under vacuum to obtain a solid product, which may exhibit waxy characteristics.

In the derivatized polymer, the relationship between portions of the derivatized polymer (e.g., poly-α(1→4)glucopyranose portion, the hydrophobic portion, and the linker portion containing the ester groups) can be expressed in various ways, such as by weight to weight ratios, by weight to molar amount ratios, and/or by molar amount to molar amount ratios.

For example, the hydrophobic portion and the poly-α (1→4)glucopyranose portion can also be expressed by the weight ratio between the two. The relationship can be calculated by comparing the amount by weight of the starting α(1→4)glucopyranose polymer to the amount by weight of the hydrophobic portion of the compound that is reacted with the α(1→4)glucopyranose polymer (i.e., the hydrocarbon segment). For purposes of discussion, the hydrophobic portion refers to the sum of the weight of all the hydrocarbon groups that contribute to the hydrophobic property of the polymer.

For example, isobutyl succinate has a molecular weight of approximately 174.2 Da, and the hydrocarbon portions (the terminal isobutyl portion and the divalent saturated two (hydro)carbon group between the ester group in the linker region) of this molecule constitutes approximately 49.5% by weight of the isobutyl succinate. In an exemplary mode of synthesis, maltodextrin is reacted with isobutyl succinate at a weight ratio of approximately 1:2.68 (5.0 g to 13.4 g). In view of a theoretically complete reaction (i.e., 100% of the isobutyl succinate reacts with hydroxyl groups on the maltodextrin) the weight ratio of the α(1→4)glucopyranose polymer (maltodextrin) to the hydrophobic portion (isobutyl hydrocarbon segment) to the is approximately 1:1.34.

In many aspects, the polysaccharide portion and the hydrophobic portion comprise the predominant portion of the hydrophobic polysaccharide. In other words, on a weight basis, the combined weight of the polysaccharide portion and the hydrophobic portion (versus the diester groups) comprise the majority of the weight of the diester-modified hydrophobic α(1→4)glucopyranose polymer.

Generally, the diester-modified hydrophobic α(1→4)glucopyranose polymer can include monomeric units of formula III: $[M^1]$-$[L^1]$-$[H^1]$, wherein $M^1$ is a monomeric unit of the poly-α(1→4)glucopyranose portion, is the distal hydrocarbon group, and $L^1$ is a linker segment that includes the two or more hydrolysable groups selected from ester and ester-containing groups. More than one (up to three) pendent groups ($[L^1]$-$[H^1]$) can be formed on a monomeric unit. Generally, the presence of a pendent group on a monomeric unit means that the monomeric unit has been "modified." The diester-modified hydrophobic α(1→4)glucopyranose polymer can also include unmodified monomeric units. A diester-modified hydrophobic α(1→4)glucopyranose polymer can also be described by the percentage (or ratio) of modified monomeric units to the unmodified monomeric units.

The pendent group ($[L^1]$-$[H^1]$) can be formed from a primary hydroxyl group on the monomeric unit, from a secondary hydroxyl group on the monomeric unit, or from both primary and secondary hydroxyl groups on the monomeric unit. In many preparations, the diester-modified hydrophobic α(1→4)glucopyranose polymer has a plurality of pendent groups wherein more primary hydroxyl groups (versus secondary hydroxyl groups) become derivatized with the pendent groups containing the hydrocarbon group and two or more ester or ester-containing groups.

In some more specific aspects, the diester-modified hydrophobic α(1→4)glucopyranose polymer can include monomeric units of formula IV: $[M^1]$-$[E^1]$-$[H^2]$-$[E^2]$-$[H^1]$, wherein $M^1$ is a monomeric unit of the poly-α(1→4)glucopyranose portion, $H^1$ is a first hydrocarbon group, and $E^1$ is a first ester or ester-containing group, $[H^2]$ is a second hydrocarbon group, and $E^2$ is a second ester or ester-containing group. In other words, formula IV is a species of formula III, wherein $[L^1]$ of formula III is $[E^1]$-$[H^2]$-$[E^2]$.

In some aspects the diester-modified hydrophobic α(1→4) glucopyranose polymer includes a derivatized monomeric unit of Formula V:

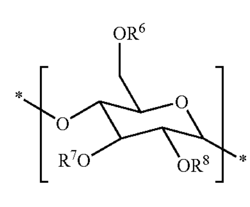

wherein one or more of $R^6$, $R^7$, and/or $R^8$ is according to formula VI:

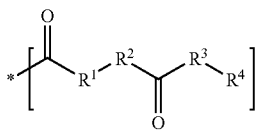

wherein $R^4$ is a $C_2$-$C_{18}$ hydrocarbon group and either:
(a) $R^1$ is $R^5$, with either (i) one or both of $R^2$ and/or $R^3$ is O (with the proviso that if only one of $R^2$ or $R^3$ is O, then the other is a covalent bond), or (ii) $R^2$ or $R^3$ is O, with the other being S; or (b) R1 is O or S, R2 is R5, R5O, or R5S, and R3 is O or S (with the proviso that if R2 is R5S or R3 is S, then R3 is O or R2 is R5O, respectively), and where, in both (a) and (b), R5 is a C1-C12 hydrocarbon group, and if one or more of R6, R7, and/or R8 is not as defined above, then one of R6, R7, and/or R8 is H.

The $C_2$-$C_{18}$ hydrocarbon group of $R^4$ can include linear, branched, or cyclic hydrocarbon structures, or combinations thereof. In some aspects, $R^4$ is a linear $C_2$-$C_{18}$ hydrocarbon group. In some aspects, $R^4$ is a branched $C_2$-$C_{18}$ hydrocarbon group. In some aspects, $R_4$ is a $C_4$-$C_{12}$ hydrocarbon group. In some aspects, $R_4$ is a $C_4$-$C_8$ hydrocarbon group.

In some aspects, $R^4$ is a partially or fully unsaturated hydrocarbon group. In some aspects, $R^4$ is a partially unsaturated hydrocarbon group.

In some aspects, $R^5$ is a partially or fully unsaturated hydrocarbon group. In some aspects, $R^5$ is a partially unsaturated hydrocarbon group.

In more specific aspects, one or more of $R^6$, $R^7$, and/or $R^8$ is according to formula VII, as follows:

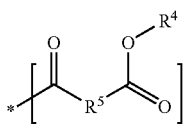

wherein $R^5$ is a divalent saturated hydrocarbon group that having one, two, or three carbon atoms, and $R^4$ is a $C_2$-$C_{18}$ hydrocarbon group, and if one or more of $R^6$, $R^7$, and/or $R^8$ is not as defined above, then one of $R^6$, $R^7$, and/or $R^8$ is H.

In more specific aspects of formula VI or formula VII, $R^5$ is a divalent saturated hydrocarbon group having two carbon atoms.

In more specific aspects of formula VII, $R^4$ is a $C_4$-$C_{12}$ hydrocarbon group. In more specific aspects of formula VII, $R^4$ is a $C_4$-$C_8$ hydrocarbon group.

In other aspects, the invention provides hydrophobic α(1→4)glucopyranose polymer having pendent groups with hydrocarbon segments and carbonate ester-containing linker segments. In some cases, the formed carbonate ester group of the linker segment replaces one or more original hydroxyl groups) on the glucopyranose monomeric unit. Pendent groups can be formed on positions on the glucopyranose monomeric units previously corresponding to either or both primary and/or secondary hydroxyl group locations. In many preparations more of the primary hydroxyl groups than secondary hydroxyl groups become derivatized with the pendent groups containing the hydrocarbon and carbonate ester groups.

In some modes of practice an α(1→4)glucopyranose polymer is reacted with one or more alkyl haloformate compound(s) to provide the pendent groups with a carbonate ester-containing linkage.

Alkyl haloformates are examples of compounds that have (a) a hydrocarbon group at one end, and a (b) hydroxyl-reactive, carbonate ester-forming group (OOCX) at the other end. Exemplary alkyl haloformates include compounds of the formula R—O(OC)X, wherein R is selected from linear, branched, or cyclic $C_1$-$C_{18}$ hydrocarbon, and X is a halogen atom, such as Cl. The linear, branched, or cyclic $C_1$-$C_{18}$ hydrocarbon group can be fully saturated, partially saturated, or fully unsaturated. In some aspects the hydrocarbon group is an alkyl group.

Exemplary alkyl groups that can be present on alkyl haloformates include, but are not limited to, methyl, ethyl, propyl, isopropyl, n-butyl, isobutyl, t-butyl, pentyl, cyclopentyl, hexyl, cyclohexyl, and octyl.

For example, suitable alkyl haloformates include, but are not limited to 2-ethylhexyl chloroformate, butenyl chloroformate, benzyl chloroformate, butyl chloroformate, cetyl chloroformate, decyl chloroformate, dodecyl chloroformate, ethyl chloroformate, hexyl chloroformate, isobutyl chloroformate, isopropenyl chloroformate, isopropyl chloroformate, neopentyl chloroformate, octyl chloroformate, and propyl chloroformate. Alkyl haloformates can be commercially obtained (for example, from Sigma Aldrich).

Generally, reaction of an alkyl haloformate with an α(1→4)glucopyranose polymer is carried out using general base catalysis. In one mode of practice, a α(1→4)glucopyranose polymer is subjected to general base catalyst to activate the hydroxyl group on the polysaccharide, forming an alkoxide ion. Next an alkyl haloformate compound is mixed with the activated polysaccharide, causing nucleophilic attack of the alkoxide ion on the alkyl haloformate to form a covalent carbonate ester linkage between the polysaccharide backbone and the alkyl group in the newly formed pendent group.

In other modes of practice, an α(1→4)glucopyranose polymer is reacted with an alkyl dicarbonate compound(s) to provide a pendent group(s).

Alkyl dicarbonates are examples of compounds that have (a) hydrocarbon groups at both ends of the molecule, and a (b) dicarbonate group between the hydrocarbon groups. Exemplary alkyl dicarbonates include compounds of the formula R'—(OC)O(CO)—R", wherein R' and R" are independently selected from linear, branched, or cyclic $C_1$-$C_{18}$ hydrocarbon. The linear, branched, or cyclic $C_1$-$C_{18}$ hydrocarbon group can be fully saturated, partially saturated, or fully unsaturated. In some aspects the hydrocarbon group is an alkyl group.

Exemplary alkyl groups that can be present in an alkyl dicarbonate include ethyl, propyl, isopropyl, n-butyl, isobutyl, t-butyl, pentyl, cyclopentyl, hexyl, cyclohexyl, and octyl.

For example, suitable alkyl dicarbonates include, but are not limited to di-tert-amyl dicarbonate, di-tent-butyl dicarbonate, dibenzyl dicarbonate, diethyl pyrocarbonate, and dimethyl dicarbonate. Alkyl dicarbonates can be commercially obtained (for example, from Sigma Aldrich).

Generally, reaction of a dicarbonate with an α(1→4)glucopyranose polymer is carried out using base (e.g., imidazole) in solvent (e.g., DMSO) at 0° C.

Compounds, such as alkyl haloformates and alkyl dicarbonates, provide pendent groups with hydrocarbon and carbonate ester groups when reacted with hydroxyl groups of the monomeric units along the length of the α(1→4)glucopyranose polymer. The derivatized α(1→4)glucopyranose polymer can include derivatized glucopyranose monomeric units having a pendent groups with hydrocarbon and carbonate ester groups, as well as underivatized glucopyranose monomeric units.

Optionally, the carbonate ester-containing hydrophobic poly(α(1→4) glucopyranose can optionally be synthesized having a combinations of pendent groups with different hydrocarbon segment chemistries. For example, the hydrophobic polysaccharide can be synthesized using a mixture of alkyl haloformates having hydrocarbon groups with different alkyl chain lengths. The carbonate ester-containing hydrophobic poly(α(1→4)glucopyranose prepared from such a mixture can be described as having first pendent groups with a particular hydrocarbon group chemistry, and second pendent groups with a particular hydrocarbon group chemistry, etc.

In preparing the hydrophobic α(1→4)glucopyranose polymer any suitable synthesis procedure can be performed. Synthesis can be carried out to provide a desired number of pendent groups containing the hydrocarbon and carbonate ester groups from the polysaccharide backbone. The number and/or density of the pendent groups can be controlled, for example, by controlling the relative concentration of the compound (e.g., an alkyl chloroformate) or compounds that provides the pendent groups to the available reactive groups (e.g., hydroxyl groups) on the polysaccharide.

The following general process outline steps describing reagent types and use of reagents in suggested ranges to provide a hydrophobic α(1→4)glucopyranose polymer. In order to provide a desired product, one of skill could modify the process by substituting the cited reagents with similar reagents, in amounts appropriate to provide a hydrophobic polysaccharide.

As an example, to provide hydrophobic poly(α(1→4)glucopyranose, butyl chloroformate (i.e., an alkyl chain length of 4) is reacted with poly(α(1→4)glucopyranose) to provide a degree of substitution of the hydroxyl groups of about 0.4 or greater, such as is in the range of about 0.4-3.0.

Preparation of a hydrophobic α(1→4)glucopyranose polymer can be carried out using a process as follows. In dry form, a molar excess of maltodextrin having a starting molecular weight in the range of about 1-500 kDa is combined with a general base catalyst. An exemplary general base catalyst is imidazole, which can be used in about 0.2-3 times the molar amount of maltodextrin. The components can then be dissolved in a polar aprotic solvent, such as DMSO, to provide a concentration of maltodextrin of approximately 100 mg/mL.

Next, a selected alkyl chloroformate (or mixture of alkyl chloroformates) is added to the activated maltodextrin mixture in an amount to provide a desired level of polysaccharide derivation. As an example, butyl chloroformate is added to the activated maltodextrin mixture in an amount of approximately 3-45 mmol (of butyl chloroformate) per gram of maltodextrin. The activated maltodextrin is then reacted with the butyl chloroformate at about room temperature for a period of time of greater than 3 days, followed by heating at 60° C. for 4 hours.

Optionally, derivation can be performed with one or more additional components that provide pendent hydrocarbon-containing groups, such as fatty acid anhydrides or alkyl succinates. Such additional optional derivation can provide pendent groups with linker segments that are different than the carbonate ester linker segments, such as linker segments that include one or more ester groups.

If reaction is carried out with two different compounds, the reaction can be performed at the same time, or can be performed sequentially.

Purification of the reaction product can be performed by the addition of water to the reaction solution, which causes precipitation of the hydrophobic α(1→4)glucopyranose polymer. The precipitated polymer can then be dried under vacuum to obtain a solid product, which may exhibit waxy characteristics.

In the derivatized polymer, the relationship between portions of the derivatized polymer (e.g., poly-α(1→4)glucopyranose portion, the hydrophobic portion, and the linker portion containing the carbonate ester groups, or two or more ester or ester containing groups) can be expressed in various ways, such as by weight to weight ratios, by weight to molar amount ratios, and/or by molar amount to molar amount ratios.

For example, the relationship between the hydrophobic portion and the poly-α(1→4)glucopyranose portion can be expressed by the weight ratio between the two. The relationship can be calculated by comparing the amount by weight of the starting α(1→4)glucopyranose polymer to the amount by weight of the hydrophobic portion of the pendent groups (e.g., the total weight of the hydrocarbon groups). The total weight of the hydrocarbon groups can be determined from the compound that is reacted with the α(1→4)glucopyranose polymer.

For example, butyl chloroformate has a molecular weight of approximately 136.58 Da (g/mol), and the hydrocarbon portion (the terminal butyl portion of the compound, which is 57 Da (g/mol)) constitutes approximately 42% by weight of the butyl chloroformate. In an exemplary mode of synthesis, maltodextrin is reacted with butyl chloroformate at a weight ratio of approximately 1:3 (10 g to 30 g). In view of a theoretically complete reaction (i.e., 100% of the butyl chloroformate reacts with hydroxyl groups on the maltodextrin) the weight ratio of the α(1→4)glucopyranose polymer (maltodextrin) to the hydrophobic portion (total butyl hydrocarbon segments) is approximately 1:2.

In some aspects, the hydrophobic α(1→4)glucopyranose polymer can include monomeric units of formula IX: $[M^2]$-$[L^2]$-$[H^2]$, wherein $M^2$ is a monomeric unit of the poly-α(1→4)glucopyranose portion, $H^2$ is a hydrocarbon group, and $L^2$ is a linker segment that includes the carbonate ester group. More than one (up to three) pendent groups ($[L^1]$-$[H^2]$) can be formed on a monomeric unit. Generally, the presence of a pendent group on a monomeric unit means that the monomeric unit has been "modified." The hydrophobic α(1→4) glucopyranose polymer can also include unmodified monomeric units. A hydrophobic α(1→4)glucopyranose polymer can also be described by the percentage (or ratio) of modified monomeric units to the unmodified monomeric units.

The pendent group ($[L^2]$-$[H^2]$) can be formed from a primary hydroxyl group on the monomeric unit (i.e., the hydroxyl group off the #6 carbon on the glucopyranose ring), from a secondary hydroxyl group on the monomeric unit (i.e., one or both of the hydroxyl group(s) of the #2 and/or #3 carbon(s) on the glucopyranose ring), or from both primary and secondary hydroxyl groups on the monomeric unit. In many preparations, the hydrophobic α(1→4)glucopyranose polymer has a plurality of pendent groups wherein more primary hydroxyl groups (versus secondary hydroxyl groups) become derivatized with the pendent groups containing the hydrocarbon segment and carbonate ester group.

In some aspects the hydrophobic α(1→4)glucopyranose polymer includes a derivatized monomeric unit of formula X:

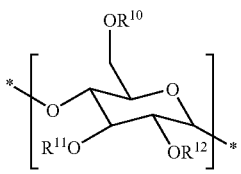

wherein one or more of $R^{10}$, $R^{11}$, and/or $R^{12}$ is according to formula XI:

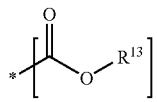

wherein, $R^{13}$ is a $C_1$-$C_{18}$ hydrocarbon group.

The $C_1$-$C_{18}$ hydrocarbon group of $R^{13}$ can include linear, branched, or cyclic hydrocarbon structures, or combinations thereof. In some aspects, $R^{13}$ is a linear $C_1$-$C_{18}$ hydrocarbon group. In some aspects, $R^{13}$ is a branched $C_3$-$C_{18}$ hydrocarbon group. In some aspects, $R^{13}$ is a $C_4$-$C_{12}$ hydrocarbon group. In some aspects, $R^{13}$ is a $C_4$-$C_8$ hydrocarbon group. In some aspects, $R^{13}$ is a $C_4$-$C_5$ hydrocarbon group.

In some aspects, $R^{13}$ is a partially or fully unsaturated hydrocarbon group. In some aspects, $R^{13}$ is a partially unsaturated hydrocarbon group.

In some aspects, a portion of the monomeric units of the hydrophobic α(1→4)glucopyranose polymer have $R^{10}$ according to formula XI. In some aspects, all of the monomeric units of the hydrophobic α(1→4)glucopyranose polymer have $R^{10}$ according to formula XI. In some aspects, all of the monomeric units of the hydrophobic α(1→4)glucopyranose polymer have $R^{10}$ according to formula XI, and a portion of the monomeric units of the hydrophobic α(1→4)glucopyranose polymer have $R^{11}$ and/or $R^{12}$ according to formula XI.

In aspects, for any $R^{10}$, $R^{11}$, and/or $R^{12}$ that are not formula XI, then $R^{10}$, $R^{11}$, and/or $R^{12}$ can be H.

In other aspects, for any $R^{10}$, $R^{11}$, and/or $R^{12}$ that are not formula XI then all or a portion of $R^{10}$, $R^{11}$, and/or $R^{12}$ can be according to formula XII.

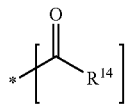

wherein, $R^{14}$ is a $C_1$-$C_{18}$ hydrocarbon group.

Optionally, the diester- or carbonate ester-modified hydrophobic poly(α(1→4) glucopyranose can include pendent groups with different linker group chemistries present on different pendent groups, and the same or a different hydrocarbon segment. The hydrophobic poly(α(1→4)glucopyranose can be described as having first pendent groups having either a diester- or carbonate ester-containing linker, and second pendent groups having a linker group that is different than the linker chemistry in the first pendent groups. The hydrophobic portion will include the total amount of hydrocarbon groups linked by all linker segments.

For example, the first set of pendent groups includes either a) two or more ester groups, or b) a carbonate ester group, such as described herein, and the second set of pendent groups includes a group selected from ester, carbonate ester, thioester, and silyl ether, with the proviso that the linker group chemistries in the first and second pendent groups are different.

In some aspects the second pendent group includes a silyl ether group. A silyl ether group, like the pendent groups with the two or more ester groups, or carbonate ester group, can display enhanced degradation in vivo.

In some aspects the hydrophobic α(1→4)glucopyranose polymer includes a derivatized monomeric unit of formula XIII:

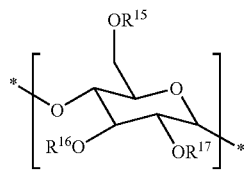

wherein one or more of $R^{15}$, $R^{16}$, and/or $R^{17}$ is according to formula VIII:

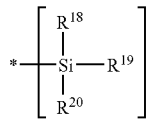

wherein one or more of $R^{18}$, $R^{19}$, and/or $R^{20}$ are independently selected from and include $C_1$-$C_{18}$ hydrocarbon groups, with the proviso that the total number of carbon atoms in $R^{18}$, $R^{18}$, and/or $R^{20}$ is at least three. Hydrophobic α(1→4)glucopyranose polymer containing these silyl ether linking groups are also described in commonly assigned and copending U.S. Application Ser. No. 61/247,402 (filed Sep. 30, 2009; Kurdyumov).

The diester- or carbonate ester-modified hydrophobic α(1→4)glucopyranose polymer is a solid material that can be processed to form a polymeric matrix in a desired form. For example, the polymer can be dissolved in a suitable solvent or may be melted when processed.

The diester- or carbonate ester-modified hydrophobic α(1→4)glucopyranose polymer has the properties of being soluble in a variety of solvents that are commonly used for dissolving hydrophobic polymers. The solubility of the diester- or carbonate ester-modified hydrophobic α(1→4) glucopyranose polymer in a solvent will depend on factors such as the level of derivation with the hydrophobic groups, as well as the particular solvent or combination of solvents used.

Exemplary solvents or dispersant include, but are not limited to, alcohols (e.g., methanol, ethanol and isopropanol), alkanes (e.g., halogenated or unhalogenated alkanes such as hexane, methylene chloride and chloroform), ethers (e.g., tetrahydrofuran (THF)), ketones (e.g., acetone, methyl ethyl ketone, methyl isobutyl ketone), aromatic compounds (e.g., toluene and xylene), nitriles (e.g., acetonitrile), and ester (e.g., ethyl acetate and butyl acetate).

Within a particular solvent, the diester- or carbonate ester-modified hydrophobic α(1→4)glucopyranose polymer may be determined to be soluble (having a solubility of at least 1 part agent per from 10 to 30 parts solvent), freely soluble (having a solubility of at least 1 part agent per from 1 to 10 parts solvent), or very soluble (having a solubility of greater than 1 part agent per 1 part solvent). These descriptive terms for solubility are standard terms used in the art (see, for example, *Remington: The Science and Practice of Pharmacy*, 20$^{th}$ ed. (2000), Lippincott Williams & Wilkins, Baltimore Md.).

The diester- or carbonate ester-modified hydrophobic α(1→4)glucopyranose polymer has the properties of being insoluble in water. The term for insolubility is a standard term used in the art, and meaning 1 part solute per 10,000 parts or greater.

In some aspects, a diester- or carbonate ester-modified hydrophobic α(1→4)glucopyranose polymer having a molecular weight within a predetermined size range is used. The molecular weight of diester- or carbonate ester-modified hydrophobic α(1→4)glucopyranose polymer can be described in terms of the starting molecular weight of the α(1→4)glucopyranose polymer, or the molecular weight of the fully derivatized polymer (i.e., including the pendent groups).

The addition of pendent groups including the hydrocarbon segment and linker portion with two or more ester or ester-containing groups, or a carbonate ester group, to the will generally cause a measurable increase in molecular weight of the poly α(1→4)glucopyranose polymer, from its underivatized, starting molecular weight. The amount increase in molecular weight can depend on one or more factors, the level of derivatization, and the chemical nature of the pendent groups.

In one aspect, the diester- or carbonate ester-modified hydrophobic α(1→4)glucopyranose polymer has a molecular weight in the range of about 5 kDa to about 5000 kDa, and in more specific aspects a molecular weight in the range of about 25 kDa to about 1000 kDa.

The diester- or carbonate ester-modified hydrophobic α(1→4)glucopyranose polymer can be present in a liquid composition including a solvent suitable to dissolve the polymer ("a polymer solvent"). Examples of solvents that can be used to prepare a composition include halogenated alkanes such as methylene chloride and chloroform. Other solvents, including aromatic compounds such as toluene and xylene, ethers such as tetrahydrofuran, and amides such as dimethylformamide (DMF), can be used to dissolve the polymer. Combinations of one or more of these or other solvents can also be used.

Compositions including dissolved diester- or carbonate ester-modified hydrophobic α(1→4)glucopyranose polymer in a solvent, or combination of solvents, can be used for the preparation of coatings, casting films, or the preparation of implantable filaments.

Diester- or carbonate ester-modified hydrophobic α(1→4) glucopyranose polymer can be provided in the form of an emulsion. For example, the diester- or carbonate ester-modified hydrophobic α(1→4)glucopyranose polymer can be present in either an oil-in-water-type of emulsion, or a water-in-oil-type of emulsion.

An oil-in-water-type of emulsion can include the diester- or carbonate ester-modified hydrophobic α(1→4)glucopyranose polymer present in the dispersed phase. An oil-in-water-type of emulsion can be prepared by dissolving the polymer in a polymer solvent such as dichloromethane, chloroform, or another solvent that is immiscible with water. The solvated polymer can be added to an excess amount of continuous phase liquid, such as water or a water-based liquid. The continuous phase liquid can include one or more additional components that can stabilize the emulsion, promote the formation of particular discontinuous phase structures.

To form a water-in-oil-type of emulsion, water or a water-based liquid can be dispersed in a continuous phase liquid such as dichloromethane or chloroform having the solubilized diester- or carbonate ester-modified hydrophobic α(1→4)glucopyranose polymer.

After the discontinuous phase and continuous phase liquids are mixed, the composition can be agitated, such as in a homogenizer, to promote emulsion formation.

The diester- or carbonate ester-modified hydrophobic α(1→4)glucopyranose polymer can be used to form articles that are wholly or partially degradable. A partially degradable article can be an article that has a biostable portion, such as a biostable body member, and a biodegradable portion, such as a biodegradable coating.

As a general matter, the method for making an implantable or injectable medical article includes steps of (a) preparing a composition comprising a hydrophobic α(1→4)glucopyranose polymer of the invention, and (b) forming a polymeric matrix from the composition, wherein the polymeric matrix is all or a portion of the implantable or injectable medical article.

The polymeric matrices formed from the diester- or carbonate ester-modified hydrophobic α(1→4)glucopyranose polymers can be used in many medical applications. These include drug delivery medical applications, as well as applications where drug delivery is not required. The applications can involve short term or long-term treatment of various conditions.

In some aspects, the diester- or carbonate ester-modified hydrophobic α(1→4)glucopyranose polymers is used to form a body member, or a portion of a body member, of an implantable medical article. In these aspects, a degradable body member, or portion thereof, can provide mechanical properties at the implantation site and can maintain these mechanical properties until they are no longer needed. After a period of time has elapsed, the body member is degraded to an extent that the mechanical properties are no longer provided, and the degraded components of the article are processed by the body.

In some embodiments, the body member of the medical article slowly degrades and transfers stress at the appropriate rate to surrounding tissues as these tissues heal and can accommodate the stress once borne by the body member of the medical article. The medical article can optionally include a coating or a bioactive agent to provide one or more additional functional features; however, these are not required in order for the article to be of use at the treatment site.

The article can also comprise filaments and fibers, such as microfibers and/or nanofibers that are formed from the diester- or carbonate ester-modified hydrophobic α(1→4) glucopyranose polymer. The filaments or fibers can be included in or associated with various articles including implantable medical articles. The filaments or fibers may be prepared with a bioactive agent to provide one or more additional functional features.

In another aspect of the invention, the diester- or carbonate ester-modified hydrophobic α(1→4)glucopyranose polymer is used to form a coated layer on a surface of a medical article. The diester- or carbonate ester-modified hydrophobic α(1→4)glucopyranose polymer can be present in one or more coated layers on all or a portion of the surface of the device. A "coating" as used herein can include one or more "coated layers", each coated layer including one or more coating materials. In some cases, the coating can be formed of a single layer of material that includes the diester- or carbonate ester-modified hydrophobic α(1→4)glucopyranose polymer. In other cases, the coating includes more than one coated layer, at least one of the coated layers including the diester- or carbonate ester-modified hydrophobic α(1→4)glucopyranose polymer. If more than one layer is present in the coating, the layers can be composed of the same or different materials.

For the formation of a coating, a composition containing the diester- or carbonate ester-modified hydrophobic α(1→4)glucopyranose polymer in a solvent system can be applied to the device surface, and then the solvent is removed from the applied composition.

The coating can also include a tie layer that promotes association of the diester- or carbonate ester-modified hydrophobic α(1→4)glucopyranose polymer with the device surface. The tie layer can be formed from any biostable or biodegradable polymer.

In some aspects, the diester- or carbonate ester-modified hydrophobic α(1→4)glucopyranose polymer is used along with a degradable polymeric tie layer material. Exemplary biodegradable tie layer polymers also include α(1→4)glucopyranose polymeric backbones.

In some aspects, the tie layer includes reactive chemistries that allow bonding of the polymer to the device surface, and/or the crosslinking of the polymer on the surface. For example, in some aspects the tie layer polymer includes a silyl ether-modified hydrophobic α(1→4)glucopyranose polymer, as described in commonly assigned U.S. patent application entitled "Silane Functionalized Hydrophobic α(1→4) Glucopyranose Polymers and Polymeric Matrices for Implantation or Injection", having Ser. No. 12/792,365 (Kurdyumov et al.; Jun. 2, 2010).

After the tie layer is formed, a composition including the diester- or carbonate ester-modified hydrophobic α(1→4) glucopyranose polymer and a bioactive agent is disposed on the polymeric tie layer, and a polymeric bioactive agent-releasing layer is formed. In the case where base layer formed from a hydrophobic α(1→4)glucopyranose polymer is used, the diester- or carbonate ester-modified hydrophobic α(1→4)glucopyranose polymer may be able to blend into the tie layer to a certain extent, thereby providing a more durable coating where the materials of the drug-releasing layer become partially mixed with the tie layer.

A coating composition (with or without bioactive agent) can be applied to a medical device using standard techniques to cover the entire surface of the device, or a portion of the device surface. If more than one coated layer is applied to a surface, it is typically applied successively. For example, a coated layer can be formed by, for example, dipping, spraying, bushing, or swabbing a coating composition including the diester- or carbonate ester-modified hydrophobic α(1→4)glucopyranose polymer on the article to form a layer, and then removing the solvent from the applied composition to form the coated layer. The process can be repeated to provide a coating having multiple coated layers, wherein at least one layer includes the diester- or carbonate ester-modified hydrophobic α(1→4)glucopyranose polymer. The compositions of the present invention are suitable for use in a spray coating processes.

An exemplary spray coating process and apparatus that can be used for coating implantable medical articles using the compositions of the present invention is described in U.S. Pat. No. 7,192,484 (Chappa et al.)

A composition that includes the diester- or carbonate ester-modified hydrophobic α(1→4)glucopyranose polymer can be spray coated directly onto the surface of a body member of a medical article, or can be spray coated onto a surface that includes one or more coated layers of material previously formed on the body member.

The following list of medical articles is provided to illustrate various medical articles that can that can be associated with a polymeric matrix made using the diester- or carbonate ester-modified hydrophobic α(1→4)glucopyranose polymer. These types of articles are typically introduced temporarily or permanently into a mammal for the prophylaxis or treatment of a medical condition. For example, these articles can be introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects the polymeric matrix made using the diester- or carbonate ester-modified hydrophobic α(1→4) glucopyranose polymer is associated with an ophthalmic article. For example, the matrix can be used as a coating on the surface of an ophthalmic article, or as a filament or drug delivery depot configured for placement at an external or internal site of the eye. In some aspects, the articles can be utilized to deliver a bioactive agent to an anterior segment of the eye (in front of the lens), and/or a posterior segment of the eye (behind the lens). Illustrative intraocular devices include, but are not limited to, those described in U.S. Pat. Nos. 6,719, 750 B2 (Varner et al.) and 5,466,233 ("Tack for Intraocular Drug Delivery and Method for Inserting and Removing Same," Weiner et al.) Illustrative ophthalmic devices for subretinal application include, but are not limited to, those described in U.S. Patent Publication No. 2005/0143363 (de Juan et al.).

A polymeric matrix made using the diester- or carbonate ester-modified hydrophobic α(1→4)glucopyranose polymer can be associated with a device formed of a non-biodegradable material. For example, a coating can be formed on a body member of a medical article that is partially or entirely fabricated from a plastic polymer. Plastic polymers include those formed of synthetic polymers, including oligomers, homopolymers, and copolymers resulting from either addition or condensation polymerizations. Examples of suitable addition polymers include, but are not limited to, acrylics (e.g., methyl acrylate) and vinyls (e.g., ethylene). Examples of condensation polymers include, but are not limited to, nylons (e.g., polycaprolactam) and also polyurethanes, polycarbonates, polyamides, polysulfones, poly(ethylene terephthalate), polydimethylsiloxanes, and polyetherketones.

The polymeric matrix can also be associated with an implantable medical article partially or entirely fabricated from a degradable polymer. The article can degrade in an aqueous environment, such as by simple hydrolysis, or can be enzymatically degraded. Examples of classes of synthetic polymers that can be used to form the structure of a degradable article include polyesters, polyamides, polyurethanes, polyorthoesters, polycaprolactone (PCL), polyiminocarbonates, aliphatic carbonates, polyphosphazenes, polyanhydrides, and copolymers thereof. As an example, the hydrophobic polysaccharide can provide a barrier coating to articles fabricated from polylactide or copolymers thereof. The coating can shield the article during a portion or all of a desired period of treatment. The coated article can still be fully degradable.

The polymeric matrix can also be associated with an implantable medical article that is partially or entirely fabricated from a metal. Although many devices or articles are constructed from substantially all metal materials, such as alloys, some may be constructed from both non-metal and metal materials, where at least a portion of the surface of the device is metal.

Commonly used metals include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

In some aspects a biodegradable coating is formed on the surface of an erodable implantable medical device formed from of a metal. For example, the biodegradable coating can be formed on a magnesium alloy stent that can be corroded following placement in a subject (see, for example, De Mario, C. et al. (2004) *J. Interv. Cardiol.*, 17(6):391-395, and Heublein, B., et al. (2003) *Heart;* 89:651-656). The erodable implantable medical device can be associated with a bioactive agent, if desired.

In aspects where the structure of the implantable medical article is fabricated from a material that is erodable or degradable, an in vivo lifetime of the article can be determined. Using the diester- or carbonate ester-modified hydrophobic $\alpha(1\rightarrow4)$glucopyranose polymer, a biodegradable coating can be formed the surface of these erodable or degradable articles to prolong their in vivo lifetime. For example, a coating formed from the diester- or carbonate ester-modified hydrophobic $\alpha(1\rightarrow4)$glucopyranose polymer can provide a hydrophobic biodegradable barrier which protects a degradable body member from degradation for a period of time. Upon degradation of the barrier, the body member can quickly degrade. The in vivo lifetime is a period of time starting upon placement of the coated article at a target location, and ending when the coated article is completely degraded at the target location.

Other contemplated biomaterials include ceramics including, but not limited to, silicon nitride, silicon carbide, zirconia, and alumina, as well as glass, silica, and sapphire. Combinations of ceramics and metals can also be coated.

The biodegradable matrix can also be associated with an article having a porous structure, such as one formed of a fabric or that has fabric-like qualities. The porous structure can be formed from textiles, which include woven materials, knitted materials, and braided materials. Particularly useful textile materials are woven materials which can be formed using any suitable weave pattern known in the art.

The porous structure can be that of a graft, sheath, cover, patch, sleeve, wrap, casing, and the like, including many of the medical articles described herein. These types of articles can function as the medical article itself or be used in conjunction with another part of a medical article.

Other particular contemplated porous structures include grafts, particularly grafts having textured exterior portions. Examples of textured grafts include those that have velour-textured exteriors, with textured or smooth interiors. Grafts constructed from woven textile products are well known in the art and have been described in numerous documents, for example, U.S. Pat. No. 4,047,252; U.S. Pat. No. 5,178,630; U.S. Pat. No. 5,282,848; and U.S. Pat. No. 5,800,514.

Bioactive agents can also be associated with a coating. The coating can include a coated layer formed using the diester- or carbonate ester-modified hydrophobic $\alpha(1\rightarrow4)$glucopyranose polymer. In some aspects, one or a combination of bioactive agents can be immobilized in a coated layer formed from the diester- or carbonate ester-modified hydrophobic $\alpha(1\rightarrow4)$glucopyranose polymer.

The term "bioactive agent," refers to an inorganic or organic molecule, which can be synthetic or natural, that causes a biological effect when administered in vivo to an animal, including but not limited to birds and mammals, including humans.

A partial list of bioactive agents is provided below. According to embodiments of the present invention, one may choose one or more of the bioactive agents to be included in an article or coating is associated with a matrix formed from the diester- or carbonate ester-modified hydrophobic $\alpha(1\rightarrow4)$glucopyranose polymer. A comprehensive listing of bioactive agents, in addition to information of the water solubility of the bioactive agents, can be found in *The Merck Index*, Thirteenth Edition, Merck & Co. (2001).

Articles and coatings prepared according to the invention can be used to release bioactive agents falling within one or more of the following bioactive agent classes. These classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, anti-proliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some cases, the hydrophobic groups pendent from the $\alpha(1\rightarrow4)$glucopyranose backbone have properties of a bioactive agent. In these aspects, the hydrophobic group/bioactive agent can be hydrolyzed from the $\alpha(1\rightarrow4)$glucopyranose backbone and released from the matrix to provide a therapeutic effect in a subject. An example of a therapeutically useful compound having a hydrocarbon segments is butyric acid, which has been shown to elicit tumor cell differentiation and apoptosis, and is thought to be useful for the treatment of cancer and other blood diseases. Other illustrative compounds comprising hydrocarbon segments include valproic acid and retinoic acid. Retinoic acid is known to possess antiproliferative effects and is thought to be useful for treatment of proliferative vitreoretinopathy (PVR). Another illustrative compound that can be coupled to the polysaccharide backbone is a corticosteroid. An exemplary corticosteroid is triamcinolone.

One method of coupling triamcinolone to a natural biodegradable polymer is by employing a modification of the method described in Cayanis, E. et al., *Generation of an Auto-anti-idiotypic Antibody that Binds to Glucocorticoid Receptor*, The Journal of Biol. Chem., 261(11): 5094-5103 (1986). Triamcinolone succinicate is prepared by reaction of triamcinolone with succinic anhydride; an acid of the resulting triamcinolone succinate is formed and then reacted with the polysaccharide, such as maltodextrin or polyalditol, resulting in pendent triamcinolone groups coupled to the polysaccharide via a linker containing two ester groups.

Thin polymer free standing films can be prepared from a composition including the diester- or carbonate ester-modified hydrophobic $\alpha(1\rightarrow4)$glucopyranose polymer. In some modes of practice, free standing films are prepared by spin casting the polymer on a glass substrate. The formed films can be floated on a water surface, and subsequently handled. The free standing films can be shaped (such as by cutting) to provide a desired configuration.

In other aspects, the diester- or carbonate ester-modified hydrophobic $\alpha(1\rightarrow4)$glucopyranose polymer is used to form an implantable or injectable medical article which also includes a bioactive agent. The implant may not have any distinct mechanical properties, such as would be apparent with an intravascular prosthesis, but rather provides a mechanism to deliver the bioactive agent to a particular portion of the body. The implant can have a defined structure and size that is appropriate for its use at a desired location in the body.

In some aspects the an implantable or injectable medical article includes a matrix formed of the diester- or carbonate ester-modified hydrophobic $\alpha(1\rightarrow4)$glucopyranose polymer which modulates the release of the bioactive agent from the article. In some cases, the matrix is in the form of a barrier layer that the bioactive agent passes through before becoming available to the subject. Such a barrier layer can be in the form of a shell of polymeric material encapsulating a core comprising bioactive agent.

In other aspect, the implant is in the form of a filament, pellet, or the like, which contains a bioactive agent. Such an implant can be formed by a process like solvent casting. A medical implant having a defined structure can be found by any suitable process, including molding, extruding, shaping, cutting, casting, and the like.

In other aspects, the diester- or carbonate ester-modified hydrophobic $\alpha(1\rightarrow4)$glucopyranose polymer is used to form a microparticle.

Microparticles including a diester- or carbonate ester-modified hydrophobic $\alpha(1\rightarrow4)$glucopyranose polymer can be formed using an oil-in-water-type emulsion process, a water-in-oil-type emulsion process, or a spray drying process. Microparticles formed using a diester- or carbonate ester-modified hydrophobic $\alpha(1\rightarrow4)$glucopyranose polymer microparticles can include a bioactive agent (such as a large biomolecule bioactive agent, like a protein). Processes such as solid (protein)/oil/water (single emulsion method), or water (aqueous protein solution)/oil/water (double emulsion method) can be used to prepare bioactive agent-containing microparticles.

In one mode of practice, diester- or carbonate ester-modified hydrophobic $\alpha(1\rightarrow4)$glucopyranose polymer-based microparticles are formed using a water/oil/water (W/O/W) emulsion solvent extraction-evaporation method based on the techniques described in Péan, J.-P. et al. (1999) *Pharma. Res.*, 16:1294-1299. The microparticles formed using this method include a bioactive agent (Péan forms microparticles including nerve growth factor using human serum albumin as a carrier). However, a bioactive agent can be included or omitted from a process based on Péan using diester- or carbonate ester-modified hydrophobic $\alpha(1\rightarrow4)$glucopyranose, as desired. In some modes of practice, if a bioactive agent is included, it is used in an amount of up to about 10% (with respect to the weight of the diester- or carbonate ester-modified hydrophobic $\alpha(1\rightarrow4)$glucopyranose polymer).

First, 0.15 mL of an aqueous phase buffered solution (e.g., 16 mM citrate buffer) and 5% human serum albumin (with respect to the amount of diester- or carbonate ester-modified hydrophobic $\alpha(1\rightarrow4)$glucopyranose used) and containing 10 µg of a polypeptide-based bioactive agent is prepared. This is then added to, and emulsified in an organic solution (e.g., about 1.2-2.0 mL of an organic solvent such as dichloromethane, ethyl acetate, chloroform, etc., or mixtures thereof) containing 500 mg of diester-modified hydrophobic $\alpha(1\rightarrow4)$glucopyranose. Emulsion is performed in a glass vial, suitable volume syringe (capped), or a thermoplastic tube (e.g., PTFE) with a lab mixer (e.g., a Silverson L4RT lab mixer with square hole head or Silverson, Model L4RT, 19 mm Tubular Head or IKA-T25 Ultra-Turrax, S 25 N-G, Coarse 8 mm diameter rotor-stater probe) for about 30-40 seconds. Mixing time can be varied based on the mixing speed and batch size or volume.

For the W/O/W (double emulsion method), after the primary emulsion is formed it is injected into a 100 mL solution of 2% PVA (in water) while homogenizing at 3000 rpm using the above-mentioned mixers for 30-40 sec. This is then poured into 600-700 mL of water, and stirred for 15 min at 300-500 rpm (using a stir-bar), followed by filtration and washing, etc.

For the solid/O/W (single emulsion method), the solid (protein) dispersed polymer solution is injected into a 100 mL solution of 2% PVA (in water) while homogenizing at 3000 rpm using the above-mentioned mixers for 30-40 sec. This is then poured into 600-700 mL of water, and stirred for 15 min at 300-500 rpm (using a stir-bar), followed by filtration and washing, etc.

Bioactive agents incorporated into the microparticles formed using these techniques can release a desired amount of the agent over a predetermined period of time. The bioactive agent can be released from the biodegradable microparticle upon degradation of the biodegradable microparticle in vivo.

Medical articles associated with a matrix formed from the diester- or carbonate ester-modified hydrophobic $\alpha(1\rightarrow4)$glucopyranose polymer can be treated to sterilize one or more parts of the article, or the entire medical article. Sterilization can take place prior to using the medical article and/or, in some cases, during implantation of the medical article.

In some aspects, the invention provides a method for delivering a bioactive agent from coating or article associated with a matrix formed from the diester- or carbonate ester-modified hydrophobic $\alpha(1\rightarrow4)$glucopyranose polymer. The bioactive agent can be present in a matrix formed from the diester- or carbonate ester-modified hydrophobic $\alpha(1\rightarrow4)$glucopyranose polymer, or associated with a different portion of the article. For example, the matrix formed from the diester- or carbonate ester-modified hydrophobic α(1→4)glucopyranose polymer may provide a barrier that the bioactive agent passes through, or the bioactive agent is releasable from a different polymeric layer that is also associated with the article.

In performing the method, the article is placed in a subject. Upon exposure to body fluid the bioactive agent is released from a portion of the article. In some cases, depending on the arrangement of the matrix formed from the diester- or carbonate ester-modified hydrophobic α(1→4)glucopyranose polymer in the article is subjected to degradation by non-enzymatic hydrolysis, enzymatic amylase activity, or both. A carbohydrase can promote the degradation of the polymeric matrix. Degradation may occur before, during, or after the release of the bioactive agent. Examples of carbohydrases that can specifically degrade natural biodegradable polysaccharide coatings include α-amylases, such as salivary and pancreatic α-amylases; disaccharidases, such as maltase, lactase and sucrase; trisaccharidases; and glucoamylase (amyloglucosidase).

Serum concentrations for amylase are estimated to be in the range of about 50-100 Upper liter, and vitreal concentrations also fall within this range (Varela, R. A., and Bossart, G. D. (2005) *J Am Vet Med Assoc* 226:88-92).

In some aspects, the carbohydrase can be administered to a subject to increase the local concentration, for example in the serum or the tissue surrounding the implanted device, so that the carbohydrase may promote the degradation of the matrix. Exemplary routes for introducing a carbohydrase include local injection, intravenous (IV) routes, and the like. Alternatively, degradation can be promoted by indirectly increasing the concentration of a carbohydrase in the vicinity of the matrix, for example, by a dietary process, or by ingesting or administering a compound that increases the systemic levels of a carbohydrase.

In other cases, the carbohydrase can be provided on a portion of the article. For example the carbohydrase may be eluted from a portion of the article that does not include the matrix. In this aspect, as the carbohydrase is released it locally acts upon the coating to cause its degradation and promote the release of the bioactive agent. The invention will be further described with reference to the following non-limiting Examples.

EXAMPLE 1

Synthesis of Isobutyl Succinate

Into a 100 mL pear-shaped round bottom flask, succinic anhydride (25 g, 250 mmol) was weighed and added. Approximately 5 mL of isobutyl alcohol was added at first. The flask was fit with a condenser and drying tube while the solution stirred magnetically. An oil bath was heated ~120° C. and the flask was placed into it. The starting material melted and the solution began refluxing. Over the next 30 minutes, 20 mL of isobutyl alcohol was added slowly. After the reaction was complete, the final solution was evaporated to dryness in vacuo and placed under vacuum to remove any traces of unreacted alcohol. $^1$HNMR in $CDCl_3$ showed the product to be 98.9% pure and the yield was quantitative.

EXAMPLE 2

Synthesis of Maltodextrin-Isobutyl Succinate

Maltodextrin M040, $MW_{ave}$ 55 kDa (5.0 g, 30.8 mmol; Grain Processing Corporation, Muscatine, Iowa) was weighed into a dry 125 mL amber jar. N-hydroxysuccinimide (NHS) (355 mg, 3.08 mmol) and N,N'-dimethylaminopyridine (DMAP) (376 mg, 3.08 mmol) were also added. The reactants were dissolved into 40 mL anhydrous DMSO and magnetically stirred at 53° C. for 10 minutes to fully dissolve all components. Once all was dissolved, the butyl succinate (13.4 g, 77.09 mmol) was added into the reaction solution, followed by N,N'-diisopropylcarbodiimide DIC) (12.8 mL, 83.26 mmol). The reaction solution was stirred at room temperature overnight.

Purification of the reaction product was performed by the addition of water to the reaction solution, which caused the precipitation of the polymer. At first, the water solution was yellow/orange in color, but as washes continued it became clear. The precipitated polymer was a sticky white wax. It was dried under vacuum overnight to obtain a sticky white solid.

EXAMPLE 3

Preparation of MD-butyl-$CO_3$ (Maltodextrin Butyl Carbonate)

A suspension of maltodextrin (10.0 g; 61.7 mmol of monomeric sugar units), 1-methylimidazole (25 mL; 307 mmol), ACN (acetonitrile; 125 mL), and water (0.5 mL; 28 mmol) was stirred overnight. To the stirred suspension was added BCF (butyl chloroformate; 45 mL; 358 mmol) at 0.25 mL/min. After the addition was complete the reaction was stirred at room temperature for 3 days. The reaction was then heated with stirring in a 60° C. water bath for 4 hours. The reaction was added to 750 mL of water in a blender. The resulting mixture was extracted with several portions of $CHCl_3$ (chloroform a total of 1 L). The $CHCl_3$ solution was dried over $Na_2SO_4$, evaporated and the residue was placed in a vacuum oven at 45° C. using a mechanical pump over night. The residue was transferred to a beaker with hot methanol (90 mL). After setting at room for more than 1 hour a sediment formed. The sediment was added to a blender containing 750 mL of water. The solid was collected on a Buchner funnel, washed with water, and dried to give 8.0 g white solid. NMR analysis of gave a butyl carbonate load of 6.23 mmol/g, which translates to a D.S. (degree of substitution) of 2.79.

EXAMPLE 4

Preparation of MD-ethyl-$CO_3$ (Maltodextrin Ethyl Carbonate)

To a solution of maltodextrin (5.0 g; 30.9 mmol of monomeric sugar units), 1-methylimidazole (7.6 g; 92.6 mmol), DMSO (dimethyl sulfoxide; 25 mL), and $CHCl_3$ (5 mL) was added diethyldicarbonate (5.0 g; 30.9 mmol) over a period of 1 hour while stirring at 0° C. The reaction solution was placed in a cold room (4° C.) over night. The reaction solution was diluted with water, placed in dialysis tubing (12-14 kDa MWCO), and dialyzed against water for 2 days. Lyophilization of the dialyzed solution gave 5.2 g of a white solid. NMR analysis gave an ethyl carbonate load of 2.06 mmol/g, which translates to a D.S. (degree of substitution) of 0.39.

EXAMPLE 5

Preparation of MD-hexanol-$CO_3$ (Maltodextrin Hexanol Carbonate)

Into an amber jar, maltodextrin (GPC, Muscatine, Iowa) was weighed and dissolved into 100 mL of anhydrous dimethyl sulfoxide (DMSO). Once dissolved, the 1,1'-carbonyldiimidazole (CDI), was weighed out and dissolved into 15 mL of DMSO. The solution was slowly added to the jar of maltodextrin solution. The reagents stirred for 20 minutes at room temperature. Hexanediol was pre-dissolved into 30 mL of DMSO and added to the reaction. The solution stirred magnetically at 55° C. overnight to react fully. The solution was then precipitated into deionized water to collect white precipitate. The powder was dried under vacuum.

What is claimed is:

1. A hydrophobic polysaccharide comprising:
a poly-α(1→4)glucopyranose portion comprising glucopyranose monomeric units, the poly-α(1→4)glucopyranose portion having a molecular weight in the range of 500 Da to 500,000 Da;
the polysaccharide comprising derivatized monomeric units of Formula V:

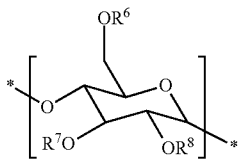

wherein at least $R^6$, and optionally $R^7$, $R^8$, or both $R^7$ and $R^8$ is according to a pendent group of Formula VI:

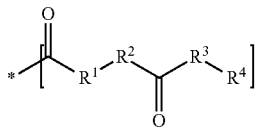

wherein $R^1$ is a $C_1$-$C_{12}$ hydrocarbon group; $R^2$ is a covalent bond; $R^3$ is O; and $R^4$ is selected from the group consisting of ethyl, propyl, isopropyl, propyl, isopropyl, n-butyl, isobutyl, t-butyl, pentyl, cyclopentyl, hexyl, and cyclohexyl, and if $R^7$ or $R^8$ is not formula VI, then $R^7$ or $R^8$ is H.

2. The hydrophobic polysaccharide of claim 1 having a degree of substitution of the pendent groups in the range of 0.5 to 2.5.

3. The hydrophobic polysaccharide of claim 1, comprising a hydrophobic portion as represented by a total weight of the hydrocarbon groups in Formula VI, wherein the poly-α (1→4)glucopyranose portion and the hydrophobic portion are present at a weight ratio in the range of 2:1 to 1:10, respectively.

4. The hydrophobic polysaccharide of claim 3 wherein the poly-α(1→4)glucopyranose portion and the hydrophobic portion are present at a weight ratio in the range of 1:1 to 1:5, respectively.

5. The hydrophobic polysaccharide of claim 1 further comprising second groups pendent from the poly-α(1→4)glucopyranose portion, the second groups comprising one or more hydrocarbon-containing group(s) linked to the monomeric units of the poly-α(1→4)glucopyranose portion via a linker segment comprising a hydrolytically cleavable group that is different than Formula VI, wherein the linker segment of the second groups comprise a group selected from the group consisting of ester, carbonate ester, thioester, silyl ether, and carbamate.

6. An implantable or injectable medical article, the article comprising a polymeric matrix comprising the hydrophobic polysaccharide of claim 1.

7. The implantable or injectable medical article of claim 6, wherein the polymeric matrix is in the form of a coating on an implantable medical device.

8. The implantable or injectable medical article of claim 6, wherein the polymeric matrix comprises a bioactive agent.

9. The hydrophobic polysaccharide of claim 1 wherein the derivatized monomeric unit of Formula V has the following structure:

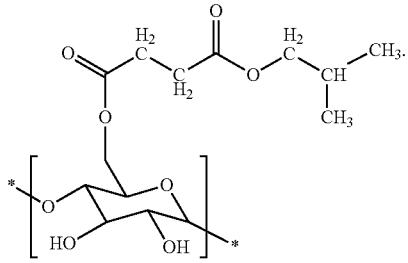

10. The hydrophobic polysaccharide of claim 1

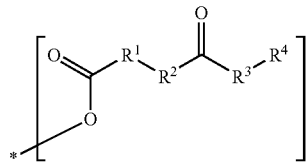

wherein $R^4$ is selected from the group consisting of propyl, isopropyl, propyl, isopropyl, n-butyl, isobutyl, and t-butyl.

11. The hydrophobic polysaccharide of claim 1 wherein $R^1$ is a divalent saturated hydrocarbon group having one, two, or three carbon atoms.

12. The hydrophobic polysaccharide of claim 1 which is soluble in methylene chloride.

13. The hydrophobic polysaccharide of claim 1 wherein the poly-α(1→4)glucopyranose portion is derived from maltodextrin.

* * * * *